United States Patent [19]

DePinho et al.

[11] Patent Number: 6,140,476
[45] Date of Patent: Oct. 31, 2000

[54] REP-MAX PROTEIN HAVING ANTI-ONCOGENIC ACTIVITY AND USES THEREOF

[75] Inventors: Ronald DePinho; Nicole Schreiber-Agus, both of New York, N.Y.

[73] Assignee: Albert Einstein College of Medicine of Yeshiva University, Bronx, N.Y.

[21] Appl. No.: 09/158,477

[22] Filed: Sep. 22, 1998

Related U.S. Application Data

[63] Continuation of application No. 08/609,046, Feb. 29, 1996, Pat. No. 5,811,298.

[51] Int. Cl.$^7$ ...................................................... C07K 5/00
[52] U.S. Cl. ............................................................ 530/402
[58] Field of Search ................................................ 530/402

*Primary Examiner*—John LeGuyaden
*Assistant Examiner*—Michael C. Wilson
*Attorney, Agent, or Firm*—Amster, Rothstein & Ebenstein

[57] ABSTRACT

The present invention provides a rep-max fusion gene which encodes a Rep-max protein capable of suppressing the oncogenic activity of a Myc family oncoprotein. The present invention further provides a vector containing nucleic acid encoding a Rep-max protein, a vector capable of expressing Rep-max protein and a recombinant viral vector capable of introducing nucleic acid encoding Rep-max protein into a target cell. Finally, the present invention provides a method for suppressing the oncogenic activity of the Myc family oncoproteins in a tumor cell and for inhibiting the growth of a tumor in a subject.

2 Claims, 4 Drawing Sheets

```
mMxi-SR   MERVRMINVQRLLEAAEFLERREREECEHGYASSFPSMPSPRLQHSKPPRR    50
mMxi-WR   -----------K--------------------------------------    14
hMxi      --------------------------------------------------    50 mMxi-SR   LSRAQKHSSGSSNTSTANRSTHNELEKNRRAHLRLCLERLKVLIPLGPDC   100
mMxi-WR   -------------------------------------------------    64
hMxi      -------------------------------------------------   100 mMxi-SR   TRHTTFGIFNKAIGHIIEFEEAERKSQHQLENLEREQRFLKRRLEQLQGP   150
mMxi-WR   -------------------------------------------------   114
hMxi      ---------------------W---------------------------   150 mMxi-SR   QEMERIRMDSIGSTISSDRSDSEREEIEVDVESTEFSHGEADSVSTTSIS   200
mMxi-WR   -------------------------------------------------   164
hMxi      -----------------------------------------V-NI----   200 mMxi-SR   DLDDHSSLQSVGSDEGYSSASVKLSFAS   228
mMxi-WR   ----------------------------   192
hMxi      -I------P-I-------------T---   228
```

FIG. 1A

REP-MAX PROTEIN HAVING ANTI-ONCOGENIC ACTIVITY AND USES THEREOF

This application is a continuation of application Ser. No. 08/609,046, filed Feb. 29, 1996, U.S. Pat. No. 5,811,298.

STATEMENT OF GOVERNMENT INTEREST

This invention was made with government support under NIH Grant Nos. EY-09300-01 and HD28317-02. As such the government has certain rights in the invention.

BACKGROUND OF THE INVENTION

Members of the myc family of nuclear proto-oncogenes (c-, N-, and L-myc) play central roles in the control of normal growth and development and in genetic pathways linked to cellular transformation and apoptotic cell death (Evan and Littlewood, Curr. Biol. 3:44–49 (1993); Morgenbesser and DePinho, Semin. Cancer Biol. 5:21–36 (1994)). Accumulating structural, biochemical, and genetic evidence affords the view that the function of Myc family oncoproteins in these diverse processes relates in part to their roles as sequence-specific transcription factors (for reviews see Kato and Dang, FASEB J. 6:30565–30572 (1992); Torres et al., Curr. Opin. Cell Biol. 4:468–474 (1992). Myc family oncoproteins appear to influence the expression of growth-promoting genes, such as those involved in DNA synthesis (Bello-Fernandez et al., Natl. Acad. Sci. USA 90:7804–7808 (1993)), and cell cycle regulation (Jansen-Durr et al., Proc. Natl. Acad. Sci, USA 90:3685–3689 (1993), in a positive manner. Myc may also play a repressive role in a regulation of some genes through interaction with an initiation factor of the general transcriptional machinery (Roy et al., Nature 365:359–361 (1993)).

Myc family proteins possess a multifunctional amino-terminal domain with transactivation potential (Kato et al., Mol. Cell. Biol. 10:5914–5920 (1990)), a region rich in basic amino acid residues responsible for sequence-specific DNA-binding activity (Blackwell et al., Science 250:1149–1151 (1990)), and a carboxy-terminal α-helical domain required for dimerization with another basic region-helix-loop-helix-leucine zipper (bHLH-LZ) protein, Max (Blackwood and Eisenman, Science 251:1211–1217 (1991); Prendergast et al., Cell 65:395–407 (1991)). Many of the biochemical and biological activities of Myc appear to be highly dependent upon its association with Max (Blackwood and Eisenman, 1991 supra; Prendergast et al., 1991 supra; Kretzner et al., Nature 359:426–4529 (1992); Amati et al., EMBO J. 12:5083–5087 (1993) and Cell 72:233–245 (1993)). In addition to its key role as an obligate partner in transactivation-competent Myc-Max complexes, Max may also repress Myc-responsive genes through the formation of transactivation-inert complexes that are capable of binding the Myc-Max recognition sequence (Blackwood et al., Genes Dev. 6:71–80 (1992); Kato et al., Genes Dev. 6:81–92 (1992); Kretzner et al., supra 1992; Makela et al., Science 256:373–376 (1992); Mukherjee et al., Genes Dev. 6:1480–1492 (1992); Prendergast et al., Genes Dev. 6:2429–2439 (1992); Ayer et al., Cell 72:211–222 (1993); Zervos et al., Cell 72:223–232 (1993)). These complexes include Max-Max homodimers, whose DNA-binding activity is subject to regulation by case in kinase II phosphorylation (Berberich and Cole, Genes Dev. 6:166–176 (1992), and the recently described hererodimers Mad-Max (Ayer et al., supra 1993) and Mxi-Max (Zervos et al., supra 1991). Together, these functionally interactive and structurally related bHLH-LZ proteins comprise an expanding Myc superfamily.

The rat embryo fibroblast (REF) cooperation assay (Land, et al., Nature 304:596–602 (1983)) has been used in order to understand the role of Myc in cell growth and the functional relationships among members of the Myc superfamily. This highly quantitative biological assay takes advantage of the ability of Myc to cooperate with activated H-RAS (Val-12) to effect the malignant transformation of early passage REFs. The REF cooperation assay has proven effective in the evaluation of candidate modulators of myc oncogenic potential, including the Max-associated proteins MAD and MXI (Lahoz et al., Proc. Natl. Acad. Sci. USA 91:5503–5507 (1994)), dominant negative mutants of Myc (Mukherjee et al., 1992 supra; Sawyers et al., Cell 70:901–910 (1992)), retinoblastoma (Rb), and other cell cycle regulators (Serrano et al., Science 267:249–252 (1995)). The functional impact of such modulators correlates well with their biochemical profiles and postulated mechanisms of action. For instance, Rb, which is thought to interact poorly with Myc in vivo. has a minimal suppressive effect on myc/RAS-induced foci formation, while over expression of MAD or MXI leads to a profound reduction in transformation activity in a highly Myc-specific manner (Lahoz et al., 1994 supra).

In the course of investigating the basis of the anti-oncogenic activity of Mxi, the inventors of the present invention identified two mxi mRNAs that arise though alternative RNA processing and that encode proteins with dramatically different abilities to repress myc-induced transformation. The capacity for strong repressive activity was found to correlate with an amino-terminal extension of 36 residues designated the Mxi "repressive domain", that is present in only one of the two Mxi protein forms. The present invention provides a fusion gene encoding a protein comprising the Mxi repressive domain and the Max bHLH-LZ and carboxy terminus which is an unexpectedly potent inhibitor of the oncogenic effect of Myc family oncoproteins.

SUMMARY OF THE INVENTION

The present invention provides a nucleic acid encoding Rep-max protein and a vector comprising nucleic acid encoding Rep-max protein. Also provided by the present invention is a recombinant viral vector comprising (a) nucleic acid of or corresponding to at least a portion of the genome of a virus which is capable of infecting a target cell, and (b) nucleic acid encoding Rep-max protein operably linked to the viral nucleic acid.

The present invention also provides a Rep-max protein.

Finally, the present invention provides a method for suppressing the oncogenic activity of a Myc family oncoprotein in a tumor cell comprising introducing nucleic acid encoding a Rep-max protein into a tumor cell such that Rep-max protein is expressed at a level sufficient to suppress the oncogenic activity of the Myc family oncoprotein as well as a method for inhibiting tumor growth in a subject comprising introducing nucleic acid encoding a Rep-max protein into substantially all the cells of a tumor such that the Rep-max protein is expressed in the cells at a level sufficient to inhibit growth of the tumor.

BRIEF DESCRIPTION OF THE FIGURES

FIGS. 1A and 1B depict a structural analysis of Mxi-SR and Mxi-WR Proteins. FIG. 1A depicts and alignment of mouse mxi-SR and mxi-WR (Schreiber-Agus et al., Cell 80:777–786 (1995)) and human MXI (Zervos et al., 1993 supra) ORF sequences. Amino acid sequences (in single-letter code) were aligned suing the Pileup program of the Genetics Computer Group sequence analysis software package (Devereuz et al., *Nucl. Acids Res.* 12:387–395 (1984)). FIG. 1B depicts schematic maps of mouse Mxi-SR, mouse Mxi-WR, human MXI, and human MAD proteins with landmark regions indicated (closed box shows repressive region). Amino acids sequences were aligned as in FIG. 1A with dashes representing residues identical to the mouse Mxi-SR residues and dots in the sequence representing gaps that were introduced to maximize homology.

FIG. 2A schematically depicts the inserts used to generate the various mxi expression constructs utilized in FIGS. 2B and 2C. The initiator codon of mxi-SR is marked by an open inverted triangle, while that of mxi-WR is marked by a closed inverted triangle. Terminator codons are marked by asterisks. (Abbreviations: Exp., experiment; ND, not determined).

DETAILED DESCRIPTION OF THE INVENTION

Figure 1B:
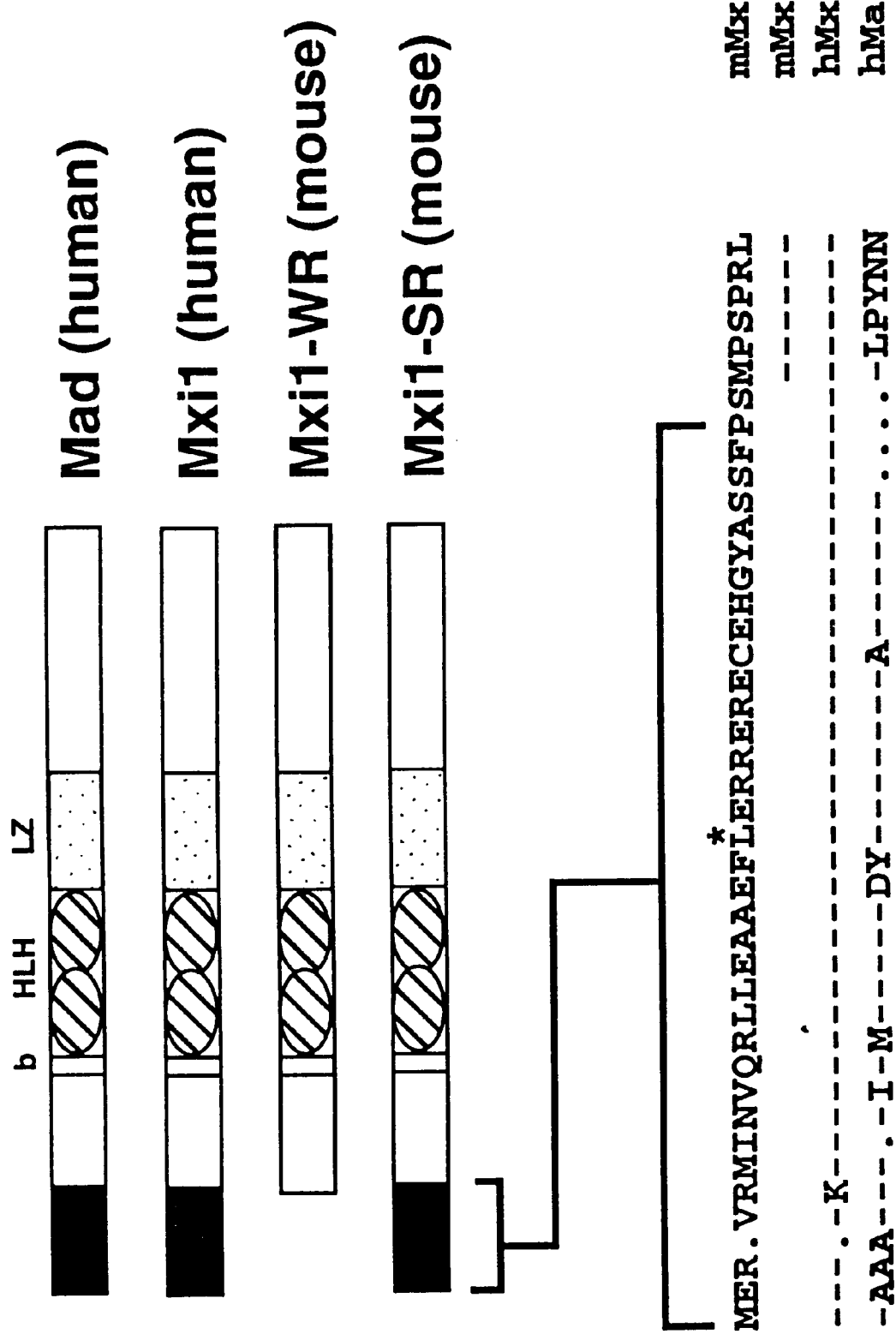

The present invention provides a rep-max fusion gene which encodes a protein, designated the "Rep-max protein", which is a potent suppressor of oncogenic activity mediated by Myc family oncoproteins. The oncogenic activity of Myc family oncoproteins has been shown to contribute to the pathogensis of numerous human neoplasms and has been implicated in the apoptotic process (Alt et al., *Cold Spring Harbor Symp. quant. Biol,* 51:9–941 (1986); Kelly and Sienbenlist, *Ann. Rev. Immun.* 4:317–338 (1986); DePinho et al., *Adv. Cancer Res.* 57:1–46 (1991), the contents of which are hereby incorporated herein in their entirety). The rep-max fusion gene of the present invention may be constructed by ligating nucleic acid encoding the "repressive domain" of Mxi in frame with nucleic acid encoding the basic (b), helix-loop-helix (HLH), leucine zipper (LZ) and carboxy terminus regions of Max. In the preferred embodiment of the present invention, the rep-max fusion gene is contained in the plasmid designated prep-max (i.e., plasmid rep-max) which was deposited under the terms of the Budapest Treaty on Feb. 29, 1996 with the American Type Culture Collection (ATCC), Rockville, Md., and assigned ATCC Accession No. 97454. Due to the degeneracy of the genetic code, the nucleic acid of the rep-max fusion gene of the present invention includes a multitude of nucleic acid substitutions which will encode the Rep-max protein.

The rep-max fusion gene of the present invention contained in prep-max was constructed by ligating the 315 base pair fragment from the Mxi-SR cDNA encoding the 5' untranslated region in addition to amino acid residues 1–70 of the Mxi-SR protein in frame to nucleic acid encoding amino acid residues 27–160 and the 3' untranslated region of Max.

The Rep-max protein encoded by the rep-max fusion gene contains the so called "repression domain" (amino acid residues 1–36 located at the amino terminal of Mxi) and up to the beginning of the basic region of Mxi joined with the basic region, helix-loop-helix, leucine zipper and carboxy terminus of Max. In the preferred embodiment, the amino acid sequence of the Rep-max protein of the present invention is encoded by the nucleic acid contained in the vector deposited under ATCC Accession No. 97454. The Rep-max protein of the present invention may be purified from cells containing a vector capable of expressing nucleic acid encoding the Rep-max protein by any one of a number of standard protein purification techniques known to one skilled in the art.

The present invention also provides a vector comprising nucleic acid encoding Rep-max protein. Such vectors may be used for storing the nucleic acid encoding Rep-max protein, or for producing large quantities Rep-max protein. The vectors may be constructed by inserting nucleic acid encoding Rep-max protein into suitable vector nucleic acid. The term "inserted" as used herein means the ligation of a foreign DNA fragment and vector DNA by techniques such as the annealing of compatible cohesive ends generated by restriction endonuclease digestion or by use of blunt end ligation techniques. Other methods of ligating DNA molecules would be apparent to one skilled in the art.

Vectors may be derived from a number of different sources. They can be plasmids, viral-derived nucleic acids, lytic bacteriophage derived from phage lambda (λ), cosmids or filamentous single-stranded bacteriophages such as M13. Depending upon the type of host cell into which the vector is introduced, vectors may be bacterial or eukaryotic. Bacterial vectors are derived from many sources including the genomes of plasmids and phage. Eukaryotic vectors are also constructed from a number of different sources, e.g. yeast plasmids and viruses. Some vectors, called shuttle vectors, are capable of replicating in both bacteria and eukaryotes. The nucleic acid from which the vector is derived is usually greatly reduced in size so that only those genes essential for its autonomous replication remain. The reduction in size enables the vectors to accommodate large segments of foreign DNA. Examples of suitable vectors into which the nucleic acid encoding the Rep-max protein of the present invention can be inserted include but are not limited to pBR322, pUC18, pHSV-106, pJS97, pJS98, M13mp18, M13mp19 , pSPORT 1, pGem, pSPORT 2, pSV.SPORT 1, pBluescript II, λZapII, λgt10, λgt11, λgt 22A, and λZIPLOX. Other suitable vectors are obvious to one skilled in the art.

The present invention also provides an expression vector comprising nucleic acid encoding Rep-max protein. As used herein, "expression" refers to the ability of the vector to transcribe the inserted nucleic acid into mRNA so that synthesis of the protein encoded by the inserted nucleic acid can occur. Bacterial and eukaryotic vectors have been engineered so that they are capable of expressing inserted nucleic acids to high levels within a host cell. Such vectors utilize one of a number of powerful promoters to direct the high level of expression. For example, eukaryotic vectors use promoter-enhancer sequences of viral genes, especially those of tumor viruses. If desired, the expression of the inserted nucleic acid can be controlled in eukaryotic cells using inducible promoters such as the metallothionine or mouse mammary tumor virus promoters.

Vectors suitable for the expression of the nucleic acid encoding the Rep-max protein are well known in the art and include pET-3d (Novagen, pProEx-1 (Life Technologies), pFastBac 1 (Life Technologies). pSFV (Life Technologies), pcDNA II (Invitrogen), pSL301 (Invitrogen), pSE280 (Invitrogen), pSE380 (Invitrogen), pSE420 (Invitrogen), pYES2 (Invitrogen), pAC360 (Invitrogen), pVL1392 and pVl1392 (Invitrogen), pCDM8 (Invitrogen), pcDNA I (Invitrogen), pcDNA I (amp) (Invitrogen), pZeoSV (Invitrogen), pcDNA 3 (Invitrogen), pRc/CMV (Invitrogen), pRc/RSV (Invitrogen), pREP4 (Invitrogen), pREP7 (Invitrogen), pREP8 (Invitrogen), pREP9 (Invitrogen), pREP10 (Invitrogen), pCEP4 (Invitrogen), pEBVHis (Invitrogen), and λPop6. Other vectors would be apparent to one skilled in the art.

The present invention also provides a recombinant viral vector for use in such applications as gene therapy. The use of recombinant viral vectors to introduce and express foreign nucleic acid in cells is well known in the art, e.g., a replication-defective recombinant adenovirus has been used to transfer the human MAD gene into human astrocytoma cells (Chen et al., *Nature Medicine* Volume 1, Number 7:638–643 (1995), the contents of which are hereby incorporated herein by reference in its entirety). The recombinant viral vector of the present invention comprises at least that portion of a viral genome which enables the virus to infect a target cell such as a tumor cell. In the recombinant vector of the present invention the viral nucleic acid sequences are operably linked to nucleic acid encoding Rep-max protein such that expression of Rep-max protein occurs upon introduction of the recombinant viral vector into the target cell. The recombinant viral vector of the present invention may further comprise specifically engineered promoter-enhancer sequences to achieve expression of the Rep-max protein localized to only a target cell and/or a high level of Rep-max protein expression in the target cell. Promoter-enhancer sequences are well known in the art and include but are not limited to herpes promoter IE 4/5. cytomegalovirus-1 promoter and the Rous sarcoma virus long terminal repeat.

Recombinant viral vectors suitable for gene therapy include but are not limited to vectors derived from the genomes of viruses such as HSV, adenovirus, adeno-associated virus, cytomegalovirus, retroviruses (infectious or replication defective), and vaccinia virus. Examples of suitable viral vectors for the introduction of nucleic acid encoding the Rep-max protein of the present invention into a target cell include but are not limited to HSVprPUC, pZeoSV (Invitrogen), pcDNA3 (Invitrogen), pRc/CMV (Invitrogen), pRc/RSV (Invitrogen), pSVT7 (Life Technologies), p91023 (B) (Life Technologies), pMB1 (Clontech), pEUK-C1 (Clontech), pMAMneo (Clontech), pMAMneo-CAT (Clontech), pMAMneo-LUC (Clontech), pDR2 (Clontech), pADα (Clontech), padβ (Clontech), pCMVβ (Clontech) and pGFP (Clontech).

The choice of recombinant viral vector will be determined by the characteristics of the target cell population, e.g., use of a recombinant viral vector which integrates into the genome of a cell such as adeno-associated virus is preferred in mitotically active cell populations such as tumor cells. Techniques for preparing stocks of recombinant viral vectors are well known in the art and may, for example, require co-infection of a "packaging cell line" with the recombinant viral vector and a helper virus. The helper virus and packaging cell line contain all the genes necessary to replicate the viral vector and package it into virions.

The present invention also provides a method for suppressing the oncogenic activity of Myc family oncoproteins of a tumor cell. The oncogenic activity of Myc family oncoproteins may arise through a number of processes, e.g., Myc family oncoproteins may positively stimulate growth-promoting genes such as those involved in DNA synthesis and cell cycle regulation. In the method of the present invention, nucleic acid encoding Rep-max protein is introduced into a tumor cell such the Rep-max protein is expressed in the cells. The Rep-max protein thus expressed suppresses the oncogenic activity of Myc family oncoproteins, by perhaps repressing the expression of Myc-responsive cell growth genes for example, and so reduces the malignant potential of the tumor cell. A suitable eukaryotic expression vector of the type discussed above, containing nucleic acid encoding Rep-max protein may be introduced into a tumor cell using a number of techniques known in the art, e.g., recombinant viral vectors of the type already discussed or transfection procedures utilizing calcium phosphate, DEAE dextran, cationic liposome fusion or electroporation.

In addition, the present invention also provides a method for inhibiting tumor growth in a subject. The ability of Rep-max protein to efficiently suppress the oncogenic activity of Myc family oncoproteins and thereby diminish the malignant potential of human neoplasms, provides a novel means of treating cancer in a human or animal subject. The method of the present invention comprises introducing nucleic acid encoding Rep-max protein into substantially all cells of a tumor in a subject such that the Rep-max protein is expressed in the tumor cells. The expression of Rep-max protein in the tumor cells inhibits tumor growth through the ability of the Rep-max protein to suppress the oncogenic activity of Myc family oncoproteins. The nucleic acid encoding the Rep-max protein may be introduced into tumor cells by any one of a number of techniques known to one skilled in the art, e.g., infecting cells with a recombinant viral vector derived from a DNA or RNA virus or a retrovirus which contains nucleic acid encoding Rep-max protein. The method of the present invention may be used to inhibit tumor growth in an embryo, newborn, infant or adult having tumors associated with a number of different malignant conditions including but not limited to melanoma, prostate cancer, glioblastoma multiforme and leukemia/lymphoma.

The following invention is described in the following Experimental Details Section, which is set forth to aid in an understanding of the invention, and should not be construed to limit in any way the invention as defined in the claims which follow thereafter.

Experimental Details Section

1. Materials and Methods

A. Isolation of Genomic and cDNA Clones and Analysis of DNA and Putative Proteins For the isolation of mouse mxi-related sequences, three human Mxi probes were used to screen at low stringency an amplified Mbol partial mouse genomic library in Charon 35A, an oligo (dT)-primed λgt10 cDNA library generated from RNA derived from MEL cell cultures 18 hr after induction with nexamethylene bisacetamide (Cheng and Skoultchi, *Mol. Cell. Biol.* 9:2332–2340 (1989)) and an oligo (dT)- and random-primed λZAPII cDNA library generated from RNA derived from mouse newborn brain (Stratagene). The human Mxi probes included a 315 bp bHLH-LZ encoding Pstl fragment, a 200 bp PCR-generated probe corresponding to the 5'-most region, and an 1100 bp Sspl fragment containing 3'UTR sequences (the human Mxi cDNA clone was provided by R. Brent (Zervos et al., 1993 supra). Purification of recombinant clones, subcloning, probe preparation and radiolabeling, and blotting and hybridizations were performed as described previously (Sambrook et al., *Cold Spring Harbor Laboratory Press* (1989)). Nucleotide sequence was determined by Sequenase (U.S. Biochemicals) and partial chemical degradation (Maxam and Gilbert, *Meth. Enzymol* 65:449–560 (1980)) and was analyzed with Genetics Computer Group sequence analysis software package (Devereuz et al., 1984 supra).

B. Expression Constructs and REF Cooperation Assays

Expression constructs for mouse mxi-WR and mouse mxi-SR were generated by placing their respective cDNAs in the sense orientation relative to two tandemly repeated Moloney murine leukemia virus long terminal repeats in pVNic (Schreiber-Agus et al., *Molec. Cell. Biol.* 13:2456–2468 (1993)), a derivative of the pVcos7 vector (Yancopoulos et al., *Proc. Natl. Acad. Sci.* USA 83:5455–5459 (1984)).

The human Mxi expression construct contained the 2.4 kb EcoRI cDNA insert described elsewhere (Zervos et al.,1993 supra) subcloned into the pVocs 7 vector in the sense orientation relative to the long terminal repeats (Lahoz et al., 1984 supra).

To make the mouse mxi-Δrep construct, a 120 bp PCI-generated fragment encoding mouse Mxi-SR 5' UTR and the first three codons of Mxi-SR was ligated in-frame to a 630 bp PCR-generated fragment that encoded amino acids 34–228 of Mxi-SR; the resultant fragment (deleted for Mxi-SR amino acids 4–33) was subcloned in pVNic in the sense orientation.

Mxi-SR-pro is identical to the mxi-SR expression construct except that Leu-19 was converted to a proline residue by PCR-based site-directed mutagenesis, a modification confirmed by nucleotide sequence analysis.

The construct rep-max was made by ligating a 315 bp EcoRI-Bglll fragment from mxi-SR containing 5' UTR and repressive region-encoding sequences in-frame to a PCR-generated 430 bp Bglll-Sall fragment from mouse max encoding its ORF from the basic region (amino acid 27 of Max) to the terminator and a 1300 bp Sall-EcoRI fragment from the mouse max 3'UTR (the template CMV-max was provided by E. Ziff); the resultant chimergic gene was subcloned into pVNic (Schreiber-Agus et al., *Cell* 80:777–786 (1995), which is hereby incorporated herein by reference in its entirety) and deposited with the ATCC under ATCC Accession No. 97454 as prep-max (i.e., plasmid rep-max).

As a control for rep-max, a 1.8 kb Hindlll-EcoRI fragment of the max cDNA encoding the MaxΔ9 protein was subcloned into pVNic. The mouse c-myc expression construct, pKO-myc (Mukherjee et al., 1992 supra), contains exons 2 and 3 of the mouse c-myc genomic clone driven by a simian virus 40 promoter/enhancer element. pT24-ras encodes the mutant H-RAS (Val-12) oncogene (Fasano et al., *J. Mol. Appl. Genet.* 2:173–180 (1983)). Early passage cultures of the REFs were prepared and cotransfected by the calcium phosphate precipitation method as described previously (Mukherjee et al., 1992 supra).

Results

A. Key Structural Features of Mouse mxi Transcripts and Putative Proteins

Low stringency hybridization to mouse cDNA libraries employing several human Mxi probes resulted in the isolation of two different cDNA clones, λmxi-SR and λmxi-WR, that differ only in their 5' regions. As shown below, the putative proteins encoded by these two cDNAs have very different abilities to antagonzie the transformation activity of Myc, hence the designations SR and WR for strong repressor and weak repressor, respectively. The organization of mouse genomic sequences encoding the 5' regions of the mxi-SR and mxi-WR cDNAs is consistent with the existence of a single mxi gene capable of producing the two mRNAs through alternative RNA processing (Schreiber-Agus et al., 1995 supra).

Nucleic acid sequence analysis of the λmxi-SR cDNA clone revealed and ATG-initiated open reading frame (ORF) capable of encoding a protein of 228 amino acids with a predicted molecular size of 25,977 Da (Mxi-SR in FIG. 1A).

That the predicted Mxi-SR protein indeed represents the mouse homolog of human Mxi-SR (Zervos et al., 1993 supra; the human MXI clone was shown to be equivalent to mouse mxi-SR and not mouse mxi-WR) is supported by their shared amino acid identity of 96% compared with only 61% when aligned with human MAD (Ayer et al., 1993 supra). The second mxi cDNA clone, λmxi-WR, is identical to λmxi-SR in the nucleic acid sequences encoding residues 37–228 of the λmxi-SR ORF and in its 3' untranslated region (3'UTR). However, the 5'-most sequences of the λmxi-SR ORF are absent from λmxi-WR and are replaced by different sequences that do not encode an in-frame ORF. As a result, the putative protein encoded by λmxi-WR would likely initiate translation at an ATG that corresponds to a methionine at position 37 in the Mxi-SR protein (Mxi-WR in FIG. 1A.

In FIG. 1A, position 1 is assigned to the putative initiation codon in the mouse Mxi-SR protein, and dashes represent residues in mouse Mxi-WR or human MXI that are identical to the mouse Mxi-SR residues. The basic region is enclosed by a box, the two helixes of the HLH region are stippled, and conserved hydrophobic residues of the LZ region are marked by open inverted triangles. With respect to the Mxi basic region, arrows indicate residues that have been shown crystallographically for Max (Ferr-D'Amare et al., *Nature* 363:38–45 (1993) and by site-directed mutagenesis for E box-binding proteins (Fisher et al., *Cell* 72:467–476 (1993), and reference therein) to confer sequence-specific DNA recognition. The conversation of Glu-76 and Arg 80 in mouse mxi-SR is integral, as these residues have been determined to contact the CG dinucleotide core of the E box specifically and thus serve to discriminate among the various CANNTG sequences. Residues that have been hypothesized to govern the selection or dismissal of dimeriztaion partners (Schreiber-Agus et al., *Oncogene* (:3167–3177 (1994)) are marked by asterisks. Specifically, the residues Arg-89 on helix 1. Lys-112 on helix 2, and Glu-123 and Glu-136 on the LZ are predicted to lie among the interacting electrostatic surface, a prediction based on the Max crystal structure (Ferre-D'Amare et al., 1993 supra) and modeling comparisons of the various Mxi proteins (Schreiber-Agus et al., 1994 supra).

the amino acid sequence of human Mxi was derived from a correction of its published nucleic acid sequence (replacement of CG residues at positions 293–294 with GGC, inversion of CG residues at positions 389–390, and deletion of TA residues at positions 894–896 of the published human Mxi cDNA sequence (Zervos et al., 1993 supra)).

B. The Mxi-SR Amino-Terminal Extension

While mxi-SR and mxi-WR ORFs encode identical bHLH-LZ and carboxy-terminal regions, alternative utilization of 5 ' sequences extends the mxi-SR ORF an additional 36 amino acids beyond the mxi-WR ORF. This extension is highly conserved throughout vertebrate evolution, exhibiting 100% similarity with human Mxi (Zervos et al., 1983 supra) and 72% similarity with zebra fish Mxi (Schreiber-Agus et al., 1994 supra) (FIG. 1B; zebra fish not shown). Notably, this region is also highly homologous (78% similar) to an analogously positioned domain in human MAD (Ayer et al., 1993 supra) (FIG. 1B). The secondary structure of this Mxi-SR amino-terminal extension is predicted to be strongly α-helical, and the potential for α helicity is conserved in the human MXI, human MAD, and zebra fish Mxi amino-terminal regions as well.

FIG. 1B shows an alignment of the domains that confer repressive activity upon mouse Mxi-SR and human MXI with a similarity positioned region in the human MAD amino terminus. This repression domain is absent from the weakly repressive Mxi-WR. The α-helical nature of this domain, as assessed by the PredictProtein algorithm (European Molecular Biology Laboratory), results from the amphipathicity of these residues. The leucine residue (Leu-19) that was converted to a proline to make Mxi-SR-pro (see Experimental Procedures) is marked by an asterisk.

Figure 2A:
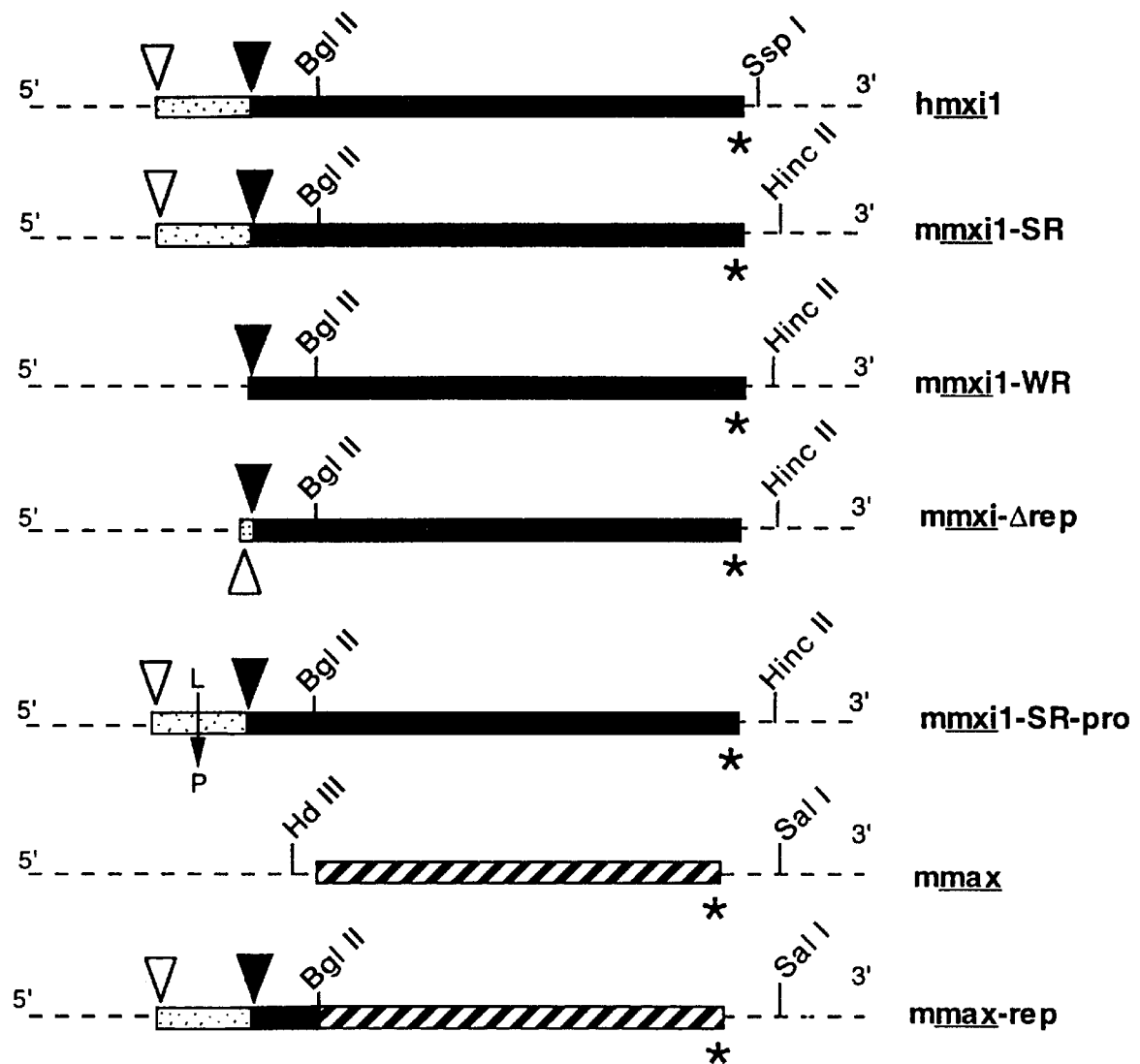
FIGS. 2A, 2B and 2C depict the structure-function analysis of various mxi constructs as assessed by anti-Myc activity in the REF assay.

Mxi-SR and Mxi-WR Have Very Different Abilities to Repress Myc Transformation Activity Human Mxi and MAD have previously been demonstrated to be potent inhibitors of myc/RAS cotransformation of REFs; this effect was shown to be Myc specific (Lahoz et al., 1994 supra). In the present study, the quantitative nature of this biological assay was exploited to determine whether mxi-SR and mxi-WR differed in their inhibitory activities. Inhibition was assessed by comparing the number of transformed foci generated in cotransfections containing mouse c-myc and activated H-RAS in the presence or absence or an equimolar amount of various mxi expression constructs in multiple independent experiments (FIG. 2) (Schreiber-Agus et al., 1995 supra).

Figures 2B, 2C:
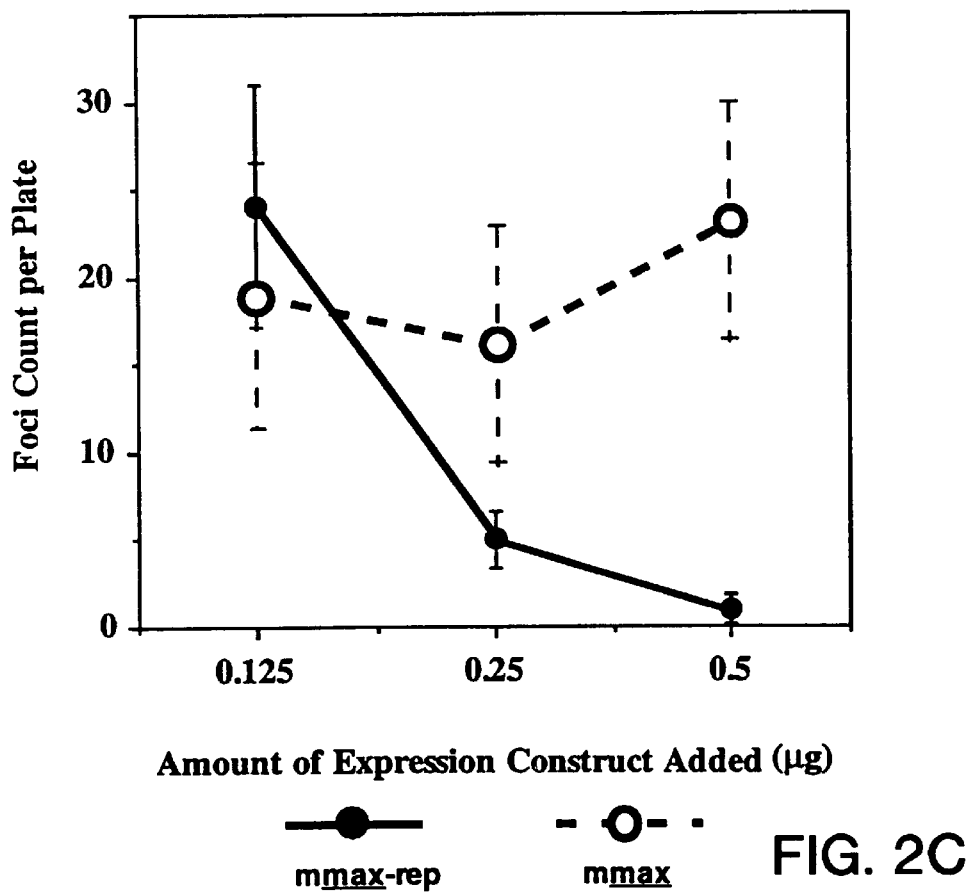

In FIG. 2B, each primary plate was transfected with 2 μg of the mouse c-myc expression construct, 2 μg of H-RAS (Val-12), 2 μg of the appropriate mxi expression construct (or empty vector) as indicated in the transfected DNA column, and 30 μg of genomic carrier DNA. The total number of foci on six plates (derived from two transfected plates that were split 1:3) was counted approximately 10 days posttransfection in five separate experiments. In FIG. 2C, each primary plate was transfected with 2 μg of c-myc, 2 μg of activated H-RAS, 30 μg of genomic carrier DNA, and the indicated amount of one of two mouse max expression constructs, i.e., one wild type and the other in which the 5' ORF sequences of max (upstream of its basic region) were replaced with those of the mxi-SR repression domain. The average number of foci per plate was determined approximately 10 days posttransfection.

In the first series of cotransfections, the mouse mxi-WR, mouse mxi-SR, and human Mxi expression constructs were compared for their ability to repress c-myc/RAS oncogenic activity. The human Mxi ORF used here was equivalent to the mouse mxi-SR form. As tabulated in FIG. 2B (experiments 1, 4 and 5), a significant reduction in the number of foci generated was observed when either mouse mxi-SR or human Mxi was added to the c-myc/RAS cotransfections; this level of suppression was comparable to that reported previously for the human Mxi gene (Lahoz et al., 1994 supra). In contrast, a similarly designed expression construct encoding mouse Mxi-WR exerted only a modest repressive effect upon c-Myc cotransformation activity, hence the suffix WR for weak repressor. On another level, when transformed cell lines were established from c-myc/RAS/mouse mxi-SR or c-myc/RAS/mouse mxi-WR foci and analyzed by Northern blotting analysis for expression of introduced genes, each showed high levels of myc- and RAS-derived transcripts, but only myc/RAS/mouse mxi-WR transformants showed abundant levels of mxi transcripts (data not shown). This observation suggests that strong selective pressure against mouse mxi-SR expression exists during progression toward the transformed state, and only those foci that fail to express the introduced mouse mxi-SR gene survive the establishment process.

In order to verify that the 5' ORF of mouse mxi-SR conferred strong repressive potential upon Mxi and to rule out the possibility that the diminished activity of mouse mxi-WR may have been due to a poor translational context of the downstream ATG, mouse mxi-Δrep, deleted in-frame for most of the putative "repression domain" of mxi-SR, was assayed in c-myc/RAS cotransfections. This construct was found to possess weak repressive potential similar to that of mxi-WR and markedly reduced from that of mxi-SR (experiments 2, 4 and 5 in FIG. 2B). Conversely, when sequences encoding the 36 resides of this domain of human Mxi were appended to the ORF of mouse mxi-WR, the resulting chimeric construct exhibited a level of repression comparable to mouse mxi-SR (data not shown). In addition, a proline for leucine substitution at position 19 of the repressive domain of Mxi-SR (see FIG. 1B) significantly diminished suppressive activity (experiments 3, 4 and 5 in FIG. 2B); since proline residues are known to cause disruptive of α-helical structures, this loss of function suggests that a α helicity may be integral to amino-terminal functions. Averaged over multiple independent experiments (representative ones employing the entire panel of mxi expression constructs are shown in experiments 4 and 5 in FIG. 2B), the fold suppression induced was 5.3 for human MXI, 8.1 for mouse Mxi-SR, 1.74 for mouse mxi-WR, 1.57 for mouse mxi-Δrep, and 1.78 for mouse Mxi-SR-pro (Schreiber-Agus et al., 1995 supra).

As these finding clearly indicated that the amino-terminal region of Mxi-SR is essential for full anti-Myc activity, its modular nature was examined further by assaying whether fusion of this domain onto Max could enhance the repressive potential of Max. It has been demonstrated that inclusion of hyermolar amounts of a max expression construct in cotransfections can inhibit transformation activity of myc family genes in the REF assay (Makela et al., 1992 supra; Mukherjee et al., 1992 supra; Prendergast et al., 1992 supra), whereas addition of submolar amounts of the max construct can act to enhance myc/RAS transforming potential slightly (Prenderhast et al., 1992 supra), presumably through the increased formation of transactivation-competent Myc-Max heterocomplexes.

Based on these observations, the impact of submolar amounts of two expression constructs, one encoding mouse Max and the other encoding a chimeric protein in which the repression domain of mxi-SR was fused in frame to the bHLH-LZ and 3' ORF sequences of mouse Max (mrep-max in FIG. 2A), was examined in the REF assay. As shown in FIG. 2C, addition of small amounts of the max expression construct did not alter the average number of foci per plate, whereas addition of the same amounts of the mouse rep-max construct exerted a profound repressive effect upon Myc cotransformation activity. Notably, in multiple experiments, the level of repression seen with the addition of an equimolar of mxi-SR to c-myc/RAS cotransfections appeared to be attained with one eighth that amount of mouse rep-max. Although the precise basis for the greatly enhanced level of repression seen with mouse rep-max remains to be determined, it may relate to the extremely stable nature of the Max protein (Blackwood et al., 1992 supra) as well as to the ability of the Max HLH-LZ region to associate with all members of Myc superfamily (Blackwood and Eisenman, *Science* 251:1211–1217 (1991); Prendergast et al., 1991 supra; Blackwood et al., 1992 supra; Ayer et al., 1993 supra; Zervos et al., 1993 supra.

That this enhanced repressive potential could have been secondary to the deletion of Max 5' ORF sequences (including phosphorylation sites) was ruled out by the finding that a construct having Mxi-WR 5' ORF sequences appended onto the same Max 3' ORF sequences present in the mouse rep-max construct did not alter the average number of foci per plate when added in the submolar amounts to myc/RAS cotransfections (data not shown).

It has also been shown that the repression domain of Mxi interacts with a transcriptional repressor called Sin3. As such, the molecular model for the suppression by Mxi of Myc involves recruitment by Mxi of a repressor that may actively prevent transcription of Myc-responsive gene targets. (Schreiber-Agus et al., 1995 supra.

All publications mentioned hereinabove are hereby incorporated by reference in their entirety.

While the foregoing invention has been described in some detail for purposes of clarity and understanding it will be appreciated by one skilled in the art from reading of the disclosure that various changes in form and detail can be made without departing from the true scope of the invention in the appended claims.

What is claimed is:

1. An isolated Rep-max fusion protein that suppresses oncogenic activity of a Myc family oncoprotein, said fusion protein comprising a mammalian Mxi repressive domain protein operatively fused to a mammalian Max bHLH-LZ protein.

2. The isolated Rep-max protein of claim 1 having an amino acid sequence encoded by the nucleic acid sequence of the vector deposited under ATCC Accession No. 97454.

* * * * *

```
                             SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
           (A) LENGTH: 228
           (B) TYPE: AMINO ACID
           (C) STRANDEDNESS: SINGLE
           (D) TOPOLOGY: LINEAR (ii) MOLECULE TYPE:
           (A) DESCRIPTION: PEPTIDE (iii) HYPOTHETICAL: YES (iv) ANTI-SENSE: NO (xi) SEQUENCE DESCRIPTION: SEQ ID NO: 1:

Met Glu Arg Val Arg Met Ile Asn Val Gln Arg Leu Leu Glu Ala
 1               5                  10                  15

Ala Glu Phe Leu Glu Arg Arg Glu Arg Glu Cys Glu His Gly Tyr
                20                  25                  30

Ala Ser Ser Phe Pro Ser Met Pro Ser Pro Arg Leu Gln His Ser
                35                  40                  45

Lys Pro Pro Arg Arg Leu Ser Arg Ala Gln Lys His Ser Ser Gly
                50                  55                  60

Ser Ser Asn Thr Ser Thr Ala Asn Arg Ser Thr His Asn Glu Leu
                65                  70                  75

Glu Lys Asn Arg Arg Ala His Leu Arg Leu Cys Leu Lys Arg Leu
                80                  85                  90

Lys Val Leu Ile Pro Leu Gly Pro Asp Cys Thr Arg His Thr Thr
                95                 100                 105

Leu Gly Leu Leu Asn Lys Ala Lys Ala His Ile Lys Lys Leu Glu
               110                 115                 120

Glu Ala Glu Arg Lys Ser Gln His Gln Leu Glu Asn Leu Glu Arg
               125                 130                 135

Glu Gln Arg Phe Leu Lys Arg Arg Leu Glu Gln Leu Gln Gly Pro
               140                 145                 150

Gln Glu Met Glu Arg Ile Arg Met Asp Ser Ile Gly Ser Thr Ile
               155                 160                 165

Ser Ser Asp Arg Ser Asp Ser Glu Arg Glu Glu Ile Glu Val Asp
               170                 175                 180

Val Glu Ser Thr Glu Phe Ser His Gly Lys Ala Asp Ser Val Ser
               185                 190                 195

Thr Thr Ser Ile Ser Asp Leu Asp Asp His Ser Ser Leu Gln Ser
               200                 205                 210
```

```
Val Gly Ser Asp Glu Gly Tyr Ser Ser Ala Ser Val Lys Leu Ser
            215                 220                 225

Phe Ala Ser (2) INFORMATION FOR SEQ ID NO:2:

(i) SEQUENCE CHARACTERISTICS:
         (A) LENGTH: 43
         (B) TYPE:  AMINO ACID
         (C) STRANDEDNESS: SINGLE
         (D) TOPOLOGY:  LINEAR (ii) MOLECULE TYPE:
         (A) DESCRIPTION:  PEPTIDE (iii) HYPOTHETICAL:  YES (iv) ANTI-SENSE:  NO (ix) FEATURE:
         (A) NAME/KEY:
         (B) LOCATION:
         (C) IDENTIFICATION METHOD:
         (D) OTHER INFORMATION:

(xi) SEQUENCE DESCRIPTION:  SEQ ID NO: 2:

Met Glu Arg Xaa Val Arg Met Ile Asn Val Gln Arg Leu Leu Glu Ala
 1               5                  10                  15

Ala Glu Phe Leu Glu Arg Arg Glu Arg Glu Cys Glu His Gly Tyr Ala
                20                  25                  30

Ser Ser Phe Pro Ser Met Pro Ser Pro Arg Leu
                35                  40

(2) INFORMATION FOR SEQ ID NO:3:

(i) SEQUENCE CHARACTERISTICS:
         (A) LENGTH: 6
         (B) TYPE:  AMINO ACID
         (C) STRANDEDNESS: SINGLE
         (D) TOPOLOGY:  LINEAR (ii) MOLECULE TYPE:
         (A) DESCRIPTION:  PEPTIDE (iii) HYPOTHETICAL:  YES (iv) ANTI-SENSE:  NO (ix) FEATURE:
         (A) NAME/KEY:
         (B) LOCATION:
         (C) IDENTIFICATION METHOD:
         (D) OTHER INFORMATION:

(xi) SEQUENCE DESCRIPTION:  SEQ ID NO: 3:

Met Pro Ser Pro Arg Leu
 1               5

(2) INFORMATION FOR SEQ ID NO:4:

(i) SEQUENCE CHARACTERISTICS:
         (A) LENGTH: 43
         (B) TYPE:  AMINO ACID
         (C) STRANDEDNESS: SINGLE
         (D) TOPOLOGY:  LINEAR (ii) MOLECULE TYPE:
         (A) DESCRIPTION:  PEPTIDE (iii) HYPOTHETICAL:  YES
```

(iv) ANTI-SENSE: NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO: 4:

Met Glu Arg Xaa Val Lys Met Ile Asn Val Gln Arg Leu Leu Glu Ala
 1               5                  10                  15

Ala Glu Phe Leu Glu Arg Arg Glu Arg Glu Cys Glu His Gly Tyr Ala
            20                  25                  30

Ser Ser Phe Pro Ser Met Pro Ser Pro Arg Leu
            35                  40

(2) INFORMATION FOR SEQ ID NO:5:

(i) SEQUENCE CHARACTERISTICS:
             (A) LENGTH: 42
             (B) TYPE: AMINO ACID
             (C) STRANDEDNESS: SINGLE
             (D) TOPOLOGY: LINEAR (ii) MOLECULE TYPE:
             (A) DESCRIPTION: PEPTIDE (iii) HYPOTHETICAL: YES (iv) ANTI-SENSE: NO (ix) FEATURE:
             (A) NAME/KEY:
             (B) LOCATION:
             (C) IDENTIFICATION METHOD:
             (D) OTHER INFORMATION:

(xi) SEQUENCE DESCRIPTION: SEQ ID NO: 5:

Met Ala Ala Ala Val Lys Met Xaa Asn Ile Gln Met Leu Leu Glu Ala
 1               5                  10                  15

Ala Asp Tyr Leu Glu Arg Arg Glu Arg Glu Ala Glu His Gly Tyr Ala
            20                  25                  30

Ser Xaa Xaa Xaa Xaa Leu Pro Tyr Asn Asn
            35                  40

(2) INFORMATION FOR SEQ ID NO:6:

(i) SEQUENCE CHARACTERISTICS:
             (A) LENGTH: 192
             (B) TYPE: AMINO ACID
             (C) STRANDEDNESS: SINGLE
             (D) TOPOLOGY: LINEAR (ii) MOLECULE TYPE:
             (A) DESCRIPTION: PEPTIDE (iii) HYPOTHETICAL: YES (iv) ANTI-SENSE: NO (xi) SEQUENCE DESCRIPTION: SEQ ID NO: 6:

Met Pro Ser Pro Arg Leu Gln His Ser Lys Pro Pro Arg Arg Leu Ser
 1               5                  10                  15

Arg Ala Gln Lys His Ser Ser Gly Ser Ser Asn Thr Ser Thr Ala Asn
            20                  25                  30

Arg Ser Thr His Asn Glu Leu Glu Lys Asn Arg Arg Ala His Leu Arg
            35                  40                  45

```
Leu Cys Leu Lys Arg Leu Lys Val Leu Ile Pro Leu Gly Pro Asp Cys
         50                  55                  60

Thr Arg His Thr Thr Leu Gly Leu Leu Asn Lys Ala Lys Ala His Ile
 65                  70                  75                  80

Lys Lys Leu Glu Glu Ala Glu Arg Lys Ser Gln His Gln Leu Glu Asn
                 85                  90                  95

Leu Glu Arg Glu Gln Arg Phe Leu Lys Arg Arg Leu Glu Gln Leu Gln
                100                 105                 110

Gly Pro Gln Glu Met Glu Arg Ile Arg Met Asp Ser Ile Gly Ser Thr
                115                 120                 125

Ile Ser Ser Asp Arg Ser Asp Ser Glu Arg Glu Glu Ile Glu Val Asp
        130                 135                 140

Val Glu Ser Thr Glu Phe Ser His Gly Lys Ala Asp Ser Val Ser Thr
145                 150                 155                 160

Thr Ser Ile Ser Asp Leu Asp Asp His Ser Ser Leu Gln Ser Val Gly
                165                 170                 175

Ser Asp Glu Gly Tyr Ser Ser Ala Ser Val Lys Leu Ser Phe Ala Ser
            180                 185                 190

(2) INFORMATION FOR SEQ ID NO:7:

(i) SEQUENCE CHARACTERISTICS:
        (A) LENGTH: 228
        (B) TYPE: AMINO ACID
        (C) STRANDEDNESS: SINGLE
        (D) TOPOLOGY: LINEAR (ii) MOLECULE TYPE:
        (A) DESCRIPTION: PEPTIDE (iii) HYPOTHETICAL: YES (iv) ANTI-SENSE: NO (xi) SEQUENCE DESCRIPTION: SEQ ID NO: 7:

Met Glu Arg Val Lys Met Ile Asn Val Gln Arg Leu Leu Glu Ala
 1               5                  10                  15

Ala Glu Phe Leu Glu Arg Arg Glu Arg Glu Cys Glu His Gly Tyr
                 20                  25                  30

Ala Ser Ser Phe Pro Ser Met Pro Ser Pro Arg Leu Gln His Ser
                 35                  40                  45

Lys Pro Pro Arg Arg Leu Ser Arg Ala Gln Lys His Ser Ser Gly
                 50                  55                  60

Ser Ser Asn Thr Ser Thr Ala Asn Arg Ser Thr His Asn Glu Leu
                 65                  70                  75

Glu Lys Asn Arg Arg Ala His Leu Arg Leu Cys Leu Lys Arg Leu
                 80                  85                  90

Lys Val Leu Ile Pro Leu Gly Pro Asp Cys Thr Arg His Thr Thr
                 95                 100                 105

Leu Gly Leu Leu Asn Lys Ala Lys Ala His Ile Lys Lys Leu Glu
                110                 115                 120

Glu Ala Glu Arg Lys Ser Gln His Gln Leu Glu Asn Leu Glu Arg
                125                 130                 135

Glu Gln Arg Phe Leu Lys Trp Arg Leu Glu Gln Leu Gln Gly Pro
                140                 145                 150

Gln Glu Met Glu Arg Ile Arg Met Asp Ser Ile Gly Ser Thr Ile
                155                 160                 165
```

-continued

```
Ser Ser Asp Arg Ser Asp Ser Glu Arg Glu Glu Ile Glu Val Asp
            170                 175                 180

Val Glu Ser Thr Glu Phe Ser His Gly Lys Val Asp Asn Ile Ser
            185                 190                 195

Thr Thr Ser Ile Ser Asp Ile Asp Asp His Ser Ser Leu Pro Ser
            200                 205                 210

Ile Gly Ser Asp Glu Gly Tyr Ser Ser Ala Ser Val Lys Leu Ser
            215                 220                 225

Phe Thr Ser
```